United States Patent [19]

Molt et al.

[11] 4,316,837
[45] Feb. 23, 1982

[54] POLYALKYLATED 4-AMINOPIPERIDINE DERIVATIVES AS STABILIZERS FOR SYNTHETIC POLYMERS

[75] Inventors: Kenneth R. Molt; Mary J. Zestermann, both of Cincinnati, Ohio

[73] Assignee: Carstab Corporation, Reading, Ohio

[21] Appl. No.: 185,822

[22] Filed: Sep. 10, 1980

[51] Int. Cl.³ .................. C07D 401/12; C08K 5/34
[52] U.S. Cl. .................. 260/45.8 N; 260/23 H; 260/45.85 B; 546/190
[58] Field of Search ............ 260/45.8 NP; 546/190

[56] References Cited

U.S. PATENT DOCUMENTS

| | | | |
|---|---|---|---|
| 3,684,765 | 8/1972 | Matsui et al. | 260/45.8 N |
| 4,110,305 | 8/1978 | Holt et al. | 260/45.8 NP |
| 4,118,368 | 10/1978 | Soma et al. | 260/45.8 NP |
| 4,166,813 | 9/1979 | Soma et al. | 260/45.8 NP |
| 4,191,683 | 3/1980 | Brunetti et al. | 546/190 |
| 4,210,576 | 7/1980 | DiBattista et al. | 546/190 |
| 4,237,294 | 12/1980 | Soma et al. | 546/20 |

*Primary Examiner*—John Kight, III
*Assistant Examiner*—R. A. White
*Attorney, Agent, or Firm*—Richard J. Sheridan; Gerald K. White

[57] ABSTRACT

Polyalkylated 4-aminopiperidine derivatives having the formula:

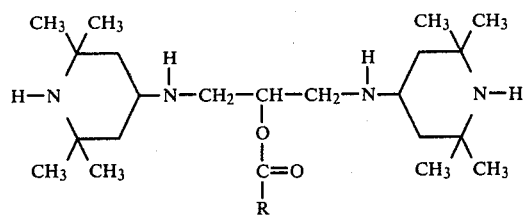

wherein R is a $C_1$–$C_{19}$ alkyl group, a cycloalkyl group of from 5 to 7 carbon atoms, an unsubstituted aryl group, an aryl group substituted with one or more $C_1$–$C_4$ alkyl or $C_1$–$C_4$ alkoxy groups, an aralkyl group having 7 or 8 carbon atoms, or

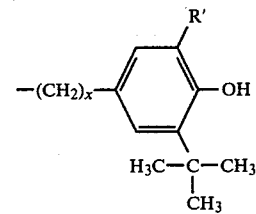

where x is an integer from 0 to 4 inclusive and R' is $C_1$–$C_4$ alkyl, which are useful as stabilizers for synthetic polymers are disclosed. Also disclosed are compositions stable to photo-deterioration comprising said polyalkylated 4-aminopiperidine derivatives and a synthetic polymer.

12 Claims, No Drawings

POLYALKYLATED 4-AMINOPIPERIDINE DERIVATIVES AS STABILIZERS FOR SYNTHETIC POLYMERS

BACKGROUND OF THE INVENTION

Various polyalkylated 4-aminopiperidine derivatives are known to be useful as light and heat stabilizers for synthetic polymers. For example, U.S. Pat. No. 3,684,765 to Matsui et al discloses 4-aminopiperidine derivatives having the formula:

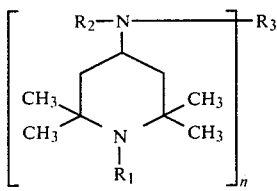

wherein $R_1$ represents hydrogen or an acyl group; $R_2$ represents hydrogen, an unsubstituted or substituted alkyl group, a cycloalkyl group, an unsubstituted or substituted aryl group, an unsubstituted or substituted aralkyl group or the group of the formula

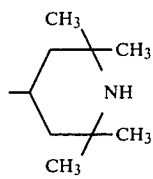

n is an integer of 1 to 3 inclusive; and, when n is 2, $R_3$ represents a diacyl group, an N-substituted dicarbamoyl group, an N-substituted bisthiocarbamoyl group, carbonyl group or a divalent group derived by removing two hydroxyl groups from an oxoacid.

U.S. Pat. No. 4,166,813 to Soma et al also discloses polymar stabilizers which are polyalkylated 4-aminopiperidine derivatives having the formula:

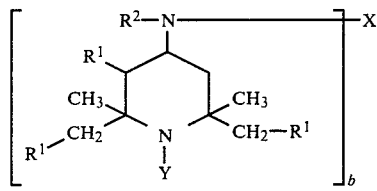

in which:
$R^1$ represents a hydrogen atom or methyl group;
$R^2$ represents a hydrogen atom or various organic radicals;
b=2 or 3; and
when b=2, X represents one of the groups of the formula

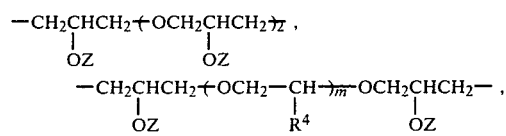

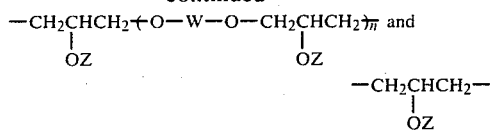

wherein m and n each represents an integer of from 1 to 10; $R^4$ represents a hydrogen atom or a methyl group; W represents various ring-containing organic radicals; Z represents a hydrogen atom or various organic radicals; with the limitation that, when $R^2$ represents a hydrogen atom,
Y represents a hydrogen atom, an alkyl group having from 1 to 18 carbon atoms, an alkenyl group having 3 or 4 carbon atoms or a benzyl group; and
Z represents a hydrogen atom.

BRIEF SUMMARY OF THE INVENTION

This invention relates to new polyalkylated 4-aminopiperidine derivatives.

More specifically, the polyalkylated 4-aminopiperidine derivatives of this invention are those compounds which have the following formula:

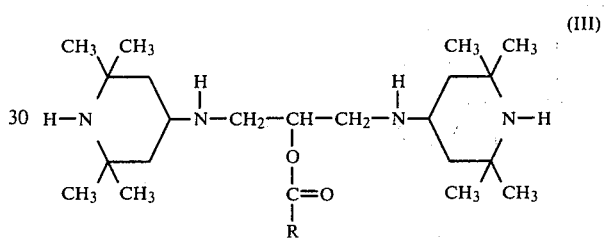

wherein R is a $C_1$-$C_{19}$ alkyl group, a cycloalkyl group of from 5 to 7 carbon atoms, an unsubstituted aryl group (aryl being phenyl, naphthyl and the like), an aryl group substituted with one or more $C_1$-$C_4$ alkyl or $C_1$-$C_4$ alkoxy groups, an aralkyl group having 7 or 8 carbon atoms, or

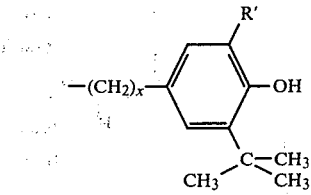

where x is an integer from 0 to 4 inclusive and R' is $C_1$-$C_4$ alkyl.

The polyalkylated 4-aminopiperidine derivatives of this invention are useful as stabilizers whose ability to protect polymers from degradation by ultraviolet (UV) radiation is superior to that of known similar stabilizers.

This invention also contemplates a polymer composition comprising a synthetic polymer and at least one of the polyalkylated 4-aminopiperidine derivatives of Formula III, in an amount sufficient to stabilize the synthetic polymer against photo-deterioration.

DESCRIPTION OF THE PREFERRED EMBODIMENTS

The polyalkylated 4-aminopiperidine derivatives of this invention can be prepared according to either of the following illustrative reaction schemes:

SCHEME A
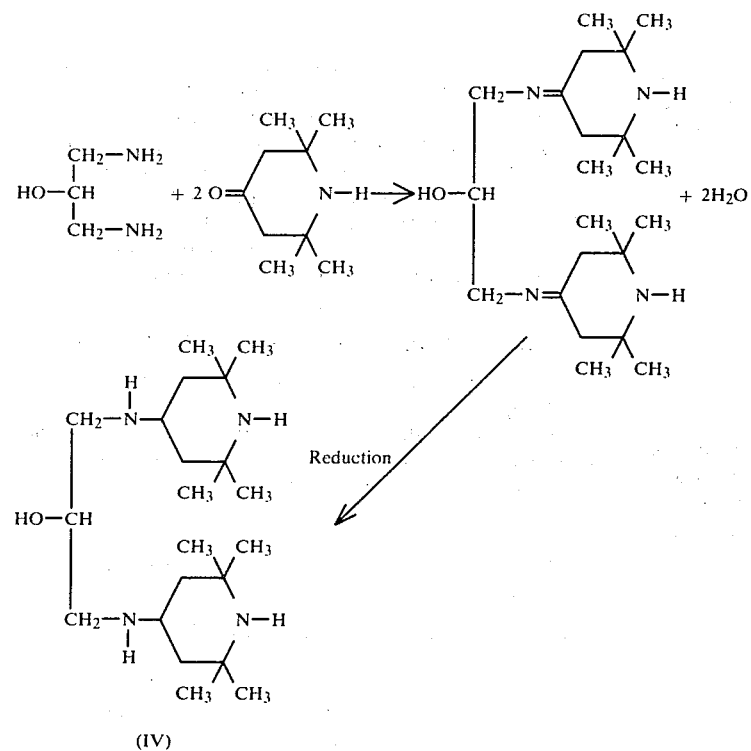
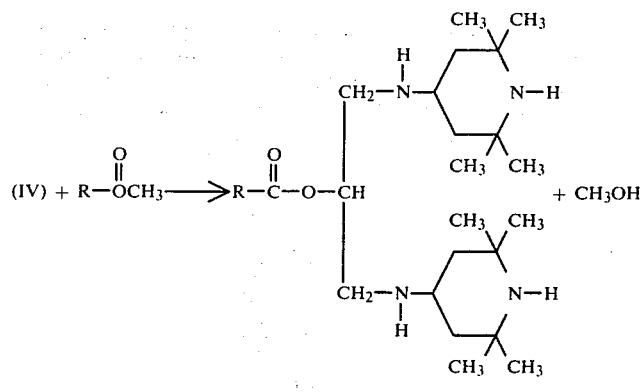
SCHEME B
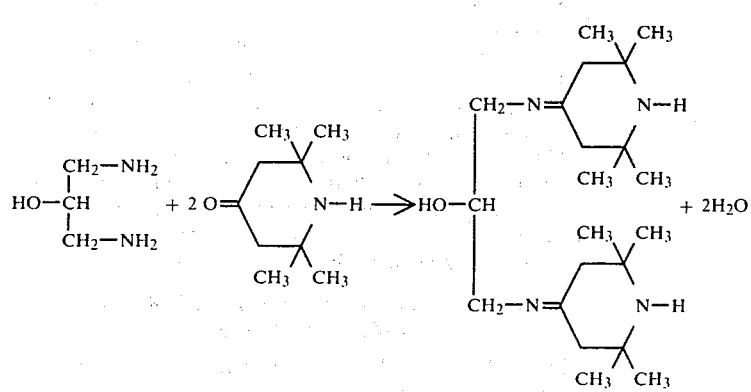

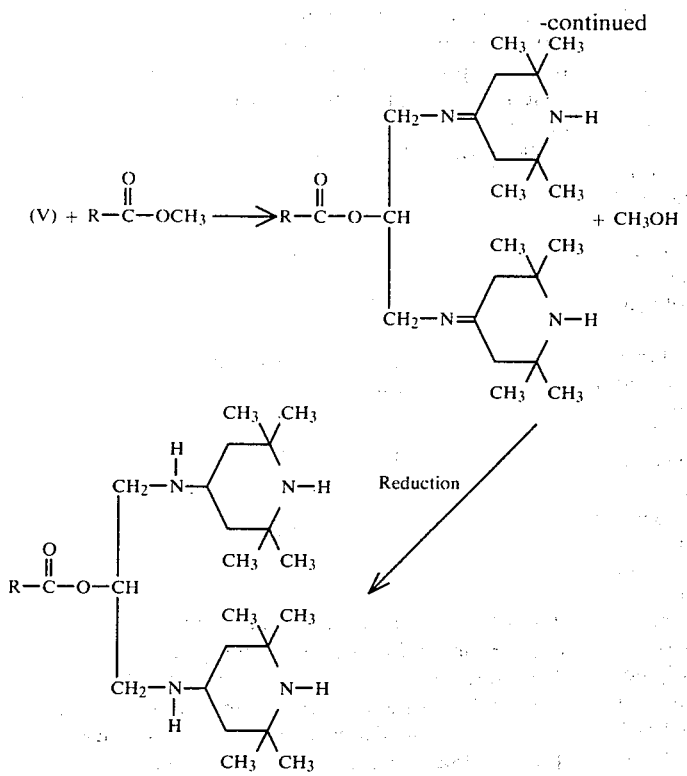

The polyalkylated 4-aminopiperidine derivatives of this invention are useful for stabilizing synthetic polymers against deterioration caused by light. Synthetic polymers which can be stabilized by the polyalkylated 4-aminopiperidine derivatives of this invention include:

olefin and diene polymers including homopolymers of olefins and dienes (e.g. low density, high density and cross-linked polyethylenes, polypropylene, polyisobutylene, polymethylbutene-1, polymethylpentene-1, polyisoprene and polybutadiene); mixtures of such homopolymers (e.g. mixtures of polypropylene with polyethylene, polypropylene with polybutene-1 or polypropylene with polyisobutylene); and copolymers of olefins and dienes (e.g. ethylene/propylene copolymers, propylene/butene-1 copolymers, propylene/isobutylene copolymers, ethylene/butene-1 copolymers and terpolymers of ethylene and propylene with such dienes as hexadiene, dicyclopentadiene or ethylidenenorbornene);

styrene polymers including polystyrene, copolymers of styrene and of α-methylstyrene (e.g. styrene/butadiene copolymers, styrene/acrylonitrile copolymers, styrene/acrylonitrile/methyl methacrylate copolymers, styrene/acrylonitrile/acrylic ester copolymers, styrene/acrylonitrile copolymers modified with acrylic ester polymers to provide impact strength, and styrene polymers modified with ethylene/propylene/diene elastomers to provide impact strength); and graft copolymers of styrene (e.g. polymers in which styrene is grafted onto polybutadiene and polymers in which styrene and acrylonitrile are grafted onto polybutadiene, as well as mixtures thereof with the aforementioned styrene copolymers—commonly known as acrylonitrile/butadiene/styrene or "ABS" plastics);

halogenated vinyl and vinylidene polymers including polyvinyl chloride, polyvinylidene chloride, polyvinyl fluoride, polychloroprene, chlorinated rubbers, vinyl chloride/vinylidene chloride copolymers, vinyl chloride/vinyl acetate copolymers and vinylidene chloride/vinyl acetate copolymers;

polymers derived from α,β-unsaturated acids and derivatives thereof, including polyacrylates and polymethacrylates, polyacrylic amides and polyacrylonitrile;

polymers derived from unsaturated alcohols and amines and from the acyl derivatives thereof or acetals, including polyvinyl alcohol, polyvinyl acetate, polyvinyl stearate, polyvinyl benzoate, polyvinyl maleate, polyvinyl butyral, polyallyl phthalate and polyallyl melamine, and copolymers thereof with other ethylenically unsaturated monomers (e.g. ethylene/vinyl acetate copolymers);

epoxy polymers including homopolymers and copolymers derived from epoxides (e.g. polyethylene oxide) and polymers derived from bis-glycidyl ethers;

polyacetals, polyalkylene oxides and polyphenylene oxides including polyoxymethylene, oxymethylene/ethylene oxide copolymers, polyoxyethylene, polypropylene oxide, polyisobutylene oxide and polyphenylene oxides;

polyurethanes and polyureas polycarbonates polysulphones polyamides and copolyamides derived from diamines and dicarboxylic acids and/or from amino-carboxylic acids or their corresponding lactams, including nylon-6, nylon-6,6, nylon-6,10, nylon-11 and nylon-12;

polyesters derived from dicarboxylic acids and dialcohols and/or from hydroxy-carboxylic acids and their corresponding lactones, e.g. polyethylene glycol terephthalate and poly-1,4-dimethylolcyclohexane terephthalate;

cross-linked polymers derived from aldehydes together with phenols, ureas or melamines, e.g. phenol/- formaldehyde, urea/formaldehyde and melamine/formaldehyde resins;

alkyd resins, e.g. glycerol/phthalic acid resins and mixtures thereof with melamine/formaldehyde resins;

unsaturated polyester resins derived from copolyesters of saturated and unsaturated dicarboxylic acids with polyhydric alcohols as well as from vinyl compounds as cross-linking agents, and also halogenated flame-resistant modifications thereof.

The amount of polyalkylated 4-aminopiperidine derivative needed to stabilize a synthetic polymer will depend upon various factors, including the type of synthetic polymer, its intended use and the presence of other additives or stabilizers, if any. Generally, however, effective stabilization is achieved when about 0.01% to about 5.0% by weight of polyalkylated 4-aminopiperidine derivative, based on the weight of the polymer, is employed. Preferably, about 0.05% to about 0.50% of stabilizer is used with polyolefin type polymers. In addition, mixtures of more than one polyalkylated 4-aminopiperidine derivative may be used.

The polyalkylated 4-amino piperidine derivatives of this invention may be incorporated into the synthetic polymer which is to be stabilized by any convenient, conventional technique. For example, the polyalkylated 4-aminopiperidine derivative and the synthetic polymer may be blended in a Henschel blender until thoroughly mixed, then the mixture can be extruded and pelletized. In order to test the effectiveness of the stabilizers, the resulting pellets may be further worked into various forms, such as extrusion into fibers or pressing into plaques.

The stabilizers of the invention can be employed as the sole stabilizer or, preferably, in combination with other conventional heat and light stabilizers for the particular synthetic polymer.

Thus, for example, in the case of polyvinyl chloride resins, other polyvinyl chloride resin heat stabilizers can be included, including polyvalent metal fatty acid salts such as barium and cadmium salts of the higher fatty acids; organic triphosphites; organotin compounds; hindered phenols; and epoxy compounds.

With polyolefin resins there can be employed fatty acid salts of polyvalent metals, organic phosphites, phenolic and thiophenolic antioxidants, and the higher fatty alcohol esters of thiodipropionic acids, such as, for example, dilauryl thiodipropionate.

With polyamide resin compositions, polyamide stabilizers such as copper salts in combination with iodides and/or phosphorus compounds and salts of divalent manganese can be used.

With synthetic rubbers and acrylonitrile-butandiene-styrene terpolymers, antioxidants such as hindered phenols and bis-phenols, polyvalent metal salts of the higher fatty acids, and organic phosphites can be used.

In addition, other conventional additives for synthetic polymers, such as plasticizers, lubricants, emulsifiers, antistatic agents, flameproofing agents, pigments and fillers, can be employed.

The following examples illustrate the preparation of the polyalkylated 4-aminopiperidine derivatives of this invention. In these examples, and throughout this specification, all parts and percentages are by weight unless otherwise indicated.

EXAMPLE 1

Triacetone amine (1.97 moles) and 1,3,-diamino-2-hydroxypropane (0.94 mole) are dissolved in 250 grams of toluene and the resulting solution is refluxed under nitrogen into a water trap for six hours. The toluene is then stripped off up to 130° C. at 15 mm Hg and the resulting crude product is crystallized from 600 grams of hexane.

The product has the structure:

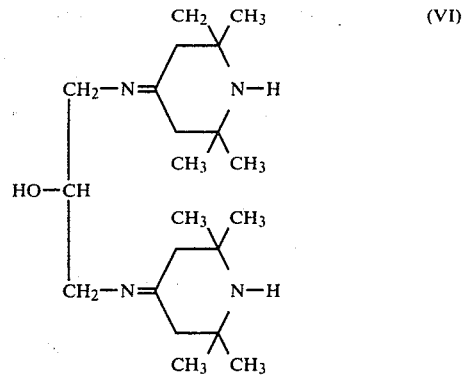

It is obtained as a white, crystalline product in a typical yield of about 277.6 grams (approximately 81.0% of theoretical yield), has a melting point of about 109°–113° C. 0.4 mole of the compound prepared above (Formula VI) is dissolved in 1600 grams of methanol. The resulting solution is cooled while 0.8 mole of $NaBH_4$ is slowly added. The temperature of the resulting reaction mixture is maintained at 30°–40° C. by cooling. After addition of the $NaBH_4$ is complete, the temperature of the reaction mixture is raised to 65° C. and maintained at that level for 30 minutes. The reaction mixture is then cooled to 20° C. and 2000 ml of water is added. The resulting mixture is distilled to remove the methanol, and 2000 ml of heptane is added. The water is then removed by azeotropic distillation into a water trap. The remaining mixture is filtered warm and the filtrate cooled to −10° C. whereupon the product crystallizes.

The product is obtained in a typical yield of about 133.0 grams (90.2% of theoretical yield) and has a melting point of about 75°–80° C. NMR and infrared analyses indicate that the product has the formula:

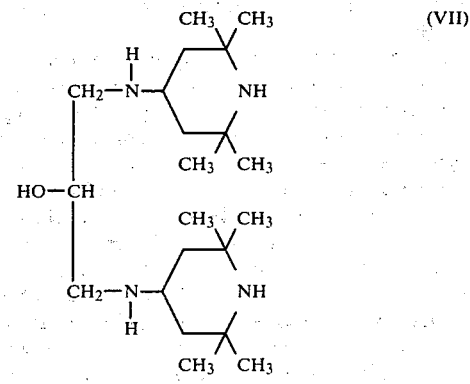

EXAMPLE 2

To 0.244 mole of the product of Example 1 (Formula VII) are added 0.244 mole of methyl-3(3,5-di-tert-butyl-4-hydroxyphenyl) propionate having the formula:

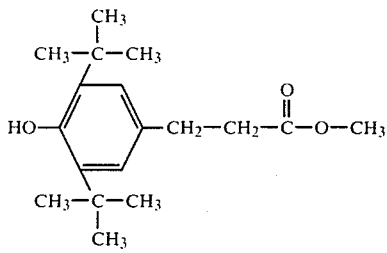

(VIII)

and 1 gram of sodium methylate catalyst. The resulting mixture is heated under nitrogen at 130° C. Methanol is evolved and heating is continued until the evolution ceases (about 6 hours). The crude product is dissolved in toluene and this solution is washed three times with water to remove the catalyst. The toluene is removed by vacuum stripping up to 150° C. at 0.5 mm Hg. The resulting product is a viscous, amber oil, obtained in a typical yield of about 152.5 grams (approximately 94.4% of theoretical yield). This amber oil crystallizes upon standing at room temperature, and the resulting crystal has a melting point of 73°–78° C. Infrared and NMR analyses of this product indicate that it has the formula:

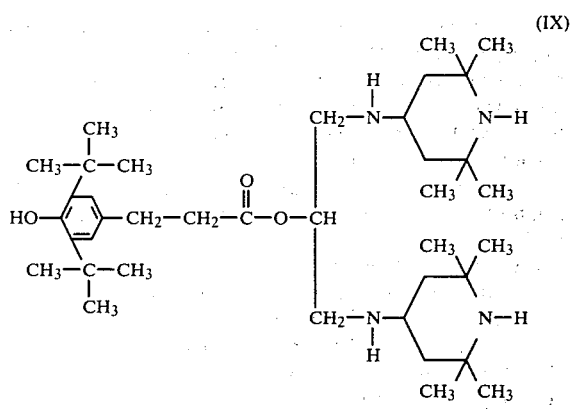

(IX)

EXAMPLE 3

The following polyalkylated 4-aminopiperidine derivative is prepared by the method of Example 2 but using methyl-β-(3-methyl-5-tert-butyl-4-hydroxyphenyl) propionate instead of methyl-3-(3,5-di-tert-butyl-4-hydroxyphenyl) propionate:

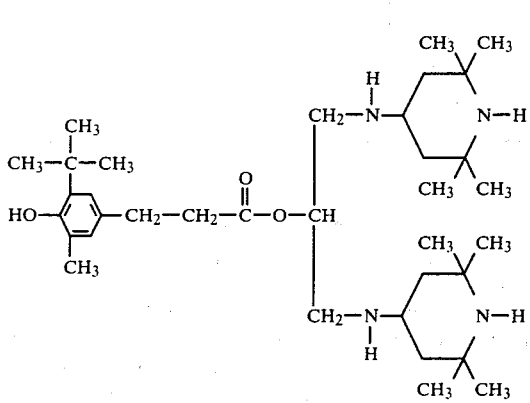

(X)

The product is an amber oil and is obtained in a typical yield of about 96.9% of theoretical yield. Infrared and NMR analyses of this product indicate that it has the above formula (X).

EXAMPLE 4

To 0.05 mole of the product of Example 1 (Formula VII) are added 0.05 mole of 3,5-di-tert-butyl-4-hydroxy methyl benzoate and 0.4 gram of sodium methylate catalyst. The resulting mixture is heated under nitrogen at 110°–160° C. for six hours during which time methanol is evolved and collected. The crude product is then dissolved in 100 grams of toluene and the resulting solution is washed three times with water to remove the catalyst. The toluene is removed by stripping up to 150° C. at 0.5 mm Hg.

The resulting product is an amber, glassy material and is obtained in a typical yield of about 30.1 grams (approximately 97.7% of theoretical yield). Infrared analyses of the product indicates its formula to be:

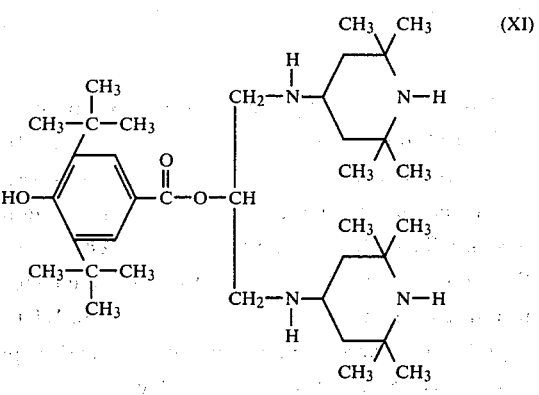

(XI)

EXAMPLE 5

The following polyalkylated 4-aminopiperidine derivative is prepared by the method of Example 2, but using ethyl acetate instead of methyl-3 (3,5-di-tert-butyl-4-hydroxyphenyl) propionate:

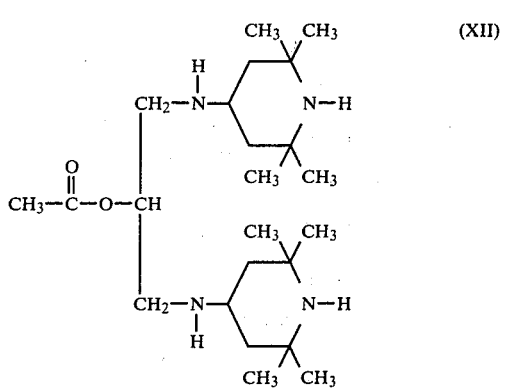

(XII)

The product is a viscous, yellow liquid. Infrared and NMR analyses of this product indicate that it has the above formula (XII).

EXAMPLE 6

The following polyalkylated 4-aminopiperidine derivative is prepared according to the method in Example 2, except that methyl stearate is used instead of methyl-3 (3,5-di-tert-butyl-4-hydroxylpheny) propionate:

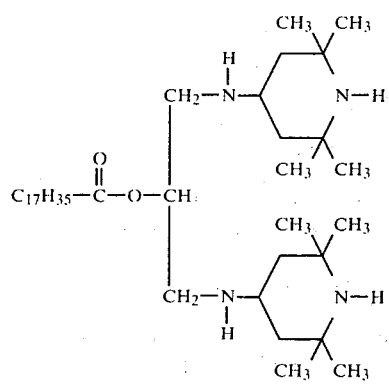

Infrared and NMR analyses indicate that the waxy product has the above formula (XIII).

EXAMPLE 7

This example is for comparison purposes only.

To 0.22 mole of the compound of Example 1 (Formula VII) are added 1.7 moles of 37% aqueous formaldehyde and 0.8 mole of formic acid. The resulting mixture is refluxed for seven hours and then cooled to 20° C. 17.6 moles of 50% aqueous NaOH is added and the resulting mixture is extracted three times with 100 ml of naphtha. The three extracts are combined and stripped of naphtha up to 160° C. at 15 mm Hg.

The resulting product is a colorless, viscous oil and is obtained in a typical yield of 91.2 grams (93.4% theoretical yield). NMR and infrared analyses indicate that the product has the formula:

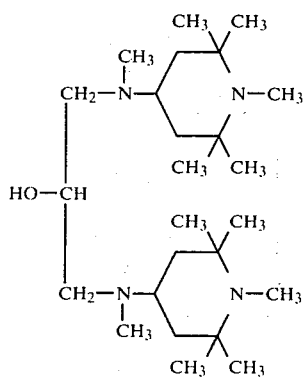

EXAMPLE 8

This example is for comparison purposes only.

The following compound is prepared by the method of Example 2 using the compound of Example 7 (Formula XIV) instead of the compound of Example 1 (Formula VII):

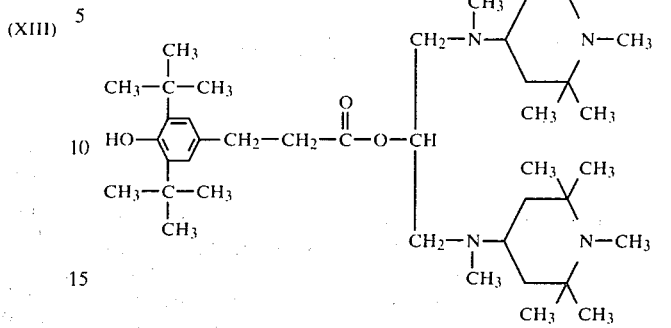

The product is a viscous amber oil and is obtained in a typical yield of 98.6% of theoretical yield. Infrared and NMR analyses indicate that the product has the above formula (XV).

The following examples illustrate the use of the polyalkylated 4-aminopiperidine derivatives of this invention to protect organic polymers from degradation by ultraviolet light.

EXAMPLE A

Several mixtures are prepared by blending 100 parts of polypropylene (Profax 6501 sold by Hercules Inc.) in a Henschel blender with 0.15 part of calcium stearate (as lubricant), 0.10 part of tetrakis [methylene (3,5-di-tert-butyl-4-hydroxyhydrocinnamate)] methane (as antioxidant and 0.5 part of each in turn of the polyalkylated 4-aminopiperidine derivatives listed in Table I. Each of the resulting mixtures are extruded and pelletized.

Each batch of the resulting pellets is extruded into fiber (20 denier per filament) and tested for tenacity on an Instron Tensile Tester. The filaments are then exposed in a Xenon Arc Weatherometer (ASTM No. D2565-76). Samples are removed at regular intervals to determine the loss in tenacity. The exposure time required for a 50% loss in the original tenacity is used to determine the fibers' stability to ultraviolet light. The results are indicated in Table I.

TABLE I

| Polyalkylated 4-aminopiperidine derivative prepared in: | Hours of Exposure of 50% Loss of Tenacity |
|---|---|
| Example 2 | 475 |
| Example 4 | 450 |
| Example 6 | 400 |
| Example 3 | 400 |
| Example 5 | 375 |
| *Example 8 | 275 |
| *Example 1 | 180 |
| *Example 7 | 160 |
| None | 25 |

*For comparison purposes only.

EXAMPLE B

Several mixtures are prepared by mixing 100 parts of high density polyethylene with 0.5 part of calcium stearate, 0.03 part of tetrakis [methylene (3,5-di-tert-butyl-4-hydroxyhydrocinnamate)] methane and 0.15 part of each in turn of the polyalkylated 4-aminopiperidine derivatives listed in Table II by milling on a two roll mill for five minutes at about 149° C.

Samples of each of the resulting mixtures are formed into 20 mil plaques by compression molding at about 177° C. and about 1000 psi for six minutes. The resulting plaques are cut into 1 inch×3 inch strips and these strips are exposed in a Xenon Arc Weatherometer (ASTM No. D2565-76). Samples are removed at regular intervals and tested for brittleness by a 180° bending test. A sample is considered to have failed if it cracks or breaks upon bending. The results are shown in Table II.

TABLE II

| Polyalkylated 4-aminopiperidine derivative prepared in: | Hours to Failure |
|---|---|
| Example 4 | 4125 |
| Example 2 | 4050 |
| Example 3 | 3925 |
| Example 6 | 3900 |
| Example 5 | 3875 |
| *Example 8 | 3075 |
| None | 250 |

*For comparison purposes only.

EXAMPLE C

Several mixtures are prepared by mixing 100 parts of polyvinyl chloride (Geon 103 sold by B. F. Goodrich Chemical Co.) with 0.5 part of dimethyltin bis-isooctylthioglycolate (thermal stabilizer), 0.5 part of stearic acid (lubricant) and 0.2 part of each in turn of the polyalkylated 4-aminopiperidine derivatives listed in Table III below. Each of the resulting mixtures is milled on a two-roll mill at about 193° C. for five minutes.

Samples of each of the resulting mixtures are formed into 20 mil plaques by compression molding at about 177° C. and about 1000 psi for six minutes. The resulting plaques are cut into 1 inch×3 inch strips. These strips, which are white in color, are exposed in a Xenon Arc Weatherometer (ASTM No. D2565-76). The colors of the plaques are noted after 400 hours of exposure. The results are indicated in Table III below.

TABLE III

| Polyalkylated 4-aminopiperidine derivative prepared in: | Plaque Color |
|---|---|
| Example 2 | Pale Yellow |
| Example 3 | Pale Yellow |
| Example 4 | Pale Yellow |
| Example 5 | Pale Yellow |
| Example 6 | Pale Yellow |
| None | Dark Yellow |

EXAMPLE D

Mixtures are prepared according to the method in Example C except that polyurethane, prepared from toluene diisocyanate and alkylene polyols, is substituted for the polyvinyl chloride. Samples containing the polyalkylated 4-aminopiperidine derivatives prepared in Examples 2, 3, 4, 5 and 6 showed much less yellowing when exposed to sunlight for one month than do samples containing no polyalkylated 4-aminopiperidine derivative.

Other features, advantages and specific embodiments of this invention will become readily apparent to those exercising ordinary skill in the art after reading the foregoing disclosures. While a few specific embodiments of this invention have been described in considerable detail, variations and modifications of these embodiments can be effected without departing from the spirit and scope of the invention as disclosed and claimed.

We claim:

1. A polymeric composition stabilized against photodeterioration comprising a synthetic polymer selected from the group consisting of olefin polymers, halogenated vinyl polymers and polyurethanes and an effective amount of a stabilizer selected from the group consisting of compounds of the formula:

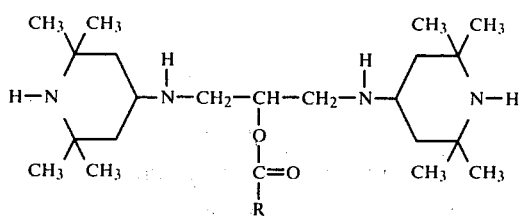

wherein R is a $C_1$-$C_{19}$ alkyl group, a cycloalkyl group of from 5 to 7 carbon atoms, an unsubstituted aryl group, an aryl group substituted with one or more $C_1$-$C_4$ alkyl or $C_1$-$C_4$ alkoxy groups, an aralkyl group having 7 or 8 carbon atoms or

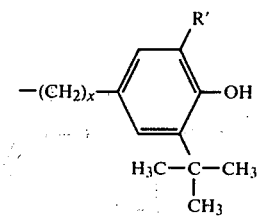

where x is an integer from 0 to 4 inclusive and R' is $C_1$-$C_4$ alkyl.

2. A polymeric composition of claim 1 wherein the synthetic polymer is an olefin polymer.

3. A polymeric composition of claim 1 wherein the synthetic polymer is a polyurethane.

4. A polymeric composition of claim 1 wherein the synthetic polymer is a polyvinyl chloride.

5. A polymeric composition of claim 1 wherein R is

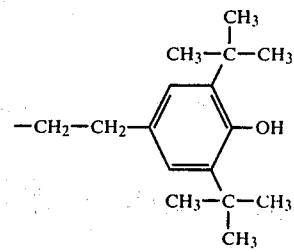

6. A polymeric composition of claim 1 wherein R is

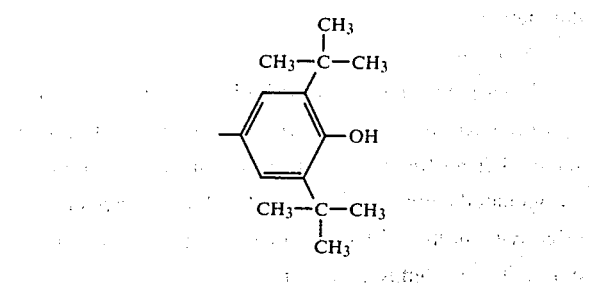

7. A polymeric composition of claim 1 wherein R is

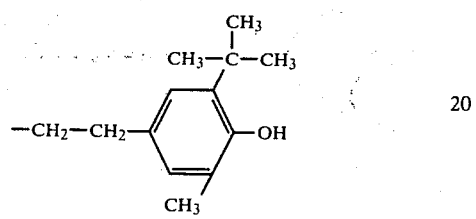

8. A polymeric composition of claim 1 wherein the stabilizer is present in amounts from about 0.01% to about 5.0% by weight, based on the weight of the polymer.

9. A compound of the formula:

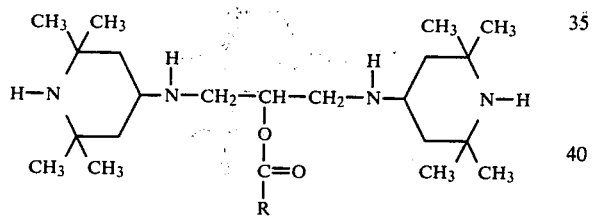

wherein R is a $C_1-C_{19}$ alkyl group, a cycloalkyl group of from 5 to 7 carbon atoms, an unsubstituted aryl group, an aryl group substituted with one or more $C_1-C_4$ alkyl or $C_1-C_4$ alkoxy groups, an aralkyl group having 7 or 8 carbon atoms, or

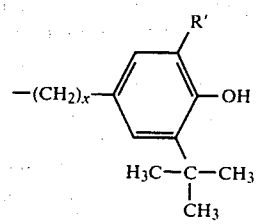

where x is an integer from 0 to 4 inclusive and R' is $C_1-C_4$ alkyl.

10. A compound of claim 9 wherein R is

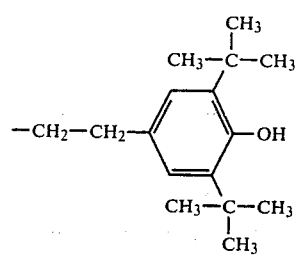

11. A compound of claim 9 wherein R is

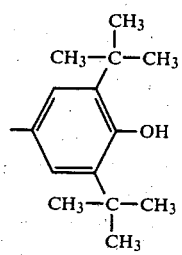

12. A compound of claim 9 wherein R is

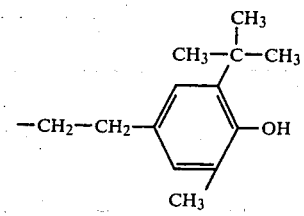

* * * * *

UNITED STATES PATENT AND TRADEMARK OFFICE
CERTIFICATE OF CORRECTION

PATENT NO. : 4,316,837
DATED : February 23, 1982
INVENTOR(S) : K. R. Molt, M. J. Zestermann It is certified that error appears in the above—identified patent and that said Letters Patent is hereby corrected as shown below:

Column 3, in the last reaction in Scheme A the formula immediately preceding the arrow should read

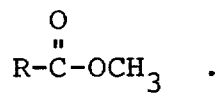

Column 7, line 52, "butandiene" should read --butadiene--.

Column 12, line 34, "tioxidant" should read --tioxidant)--.

Signed and Sealed this

Eighteenth Day of May 1982

[SEAL]

Attest:

*Attesting Officer*

GERALD J. MOSSINGHOFF
*Commissioner of Patents and Trademarks*